(12) United States Patent
Sartawi

(10) Patent No.: US 10,149,774 B1
(45) Date of Patent: Dec. 11, 2018

(54) METHOD OF PERFORMING A MODIFIED INTERVASTUS APPROACH IN TOTAL KNEE ARTHROPLASTY PROCEDURES

(71) Applicant: Muthana Sartawi, Safat (KW)

(72) Inventor: Muthana Sartawi, Safat (KW)

( * ) Notice: Subject to any disclaimer, the term of this patent is extended or adjusted under 35 U.S.C. 154(b) by 0 days.

(21) Appl. No.: 15/926,669

(22) Filed: Mar. 20, 2018

(51) Int. Cl.
*A61F 2/38* (2006.01)
*A61F 2/46* (2006.01)

(52) U.S. Cl.
CPC ............... *A61F 2/461* (2013.01); *A61F 2/38* (2013.01)

(58) Field of Classification Search
CPC ...................................... A61F 2/461
See application file for complete search history.

(56) References Cited

U.S. PATENT DOCUMENTS

| 5,947,913 | A | 9/1999 | Palumbo | |
|---|---|---|---|---|
| 2014/0228963 | A1 | 8/2014 | Bonutti | |
| 2018/0064547 | A1* | 3/2018 | Greiwe | .............. A61B 17/1684 |

FOREIGN PATENT DOCUMENTS

RU 2363404 C2 8/2009

OTHER PUBLICATIONS

Vaishya et al., "Surgical approaches for total knee arthroplasty," J Clin Orthop Trauma, 7(2): 71-79, 2016, published online Dec. 3, 2015, retrieved from https://www.ncbi.nlm.nih.gov/pmc/articles/PMC4857169/[Sep. 5, 2018].*
Sartawi et al., "Modified Intervastus Approach to the Knee," J Knee Surg., Jul. 12, 2017.

* cited by examiner

*Primary Examiner* — Thomas J Sweet
*Assistant Examiner* — Megan Wolf
(74) *Attorney, Agent, or Firm* — Richard C. Litman

(57) ABSTRACT

In the method of performing a modified intervastus approach in total knee arthroplasty procedures, a straight incision is initially made in a patient's knee. The incision is located medial to a midline of the patient's knee, in line with the medial border of the tibial tubercle distally extending proximal to the patient's patella. Fascia overlying a lateral edge of the patient's vastus medialis is then incised at a point where the patient's vastus medialis meets the patient's quadriceps tendon. The patient's vastus medialis is separated from the patient's quadriceps tendon and the patient's vastus medialis is elevated off of an underlying capsule. The underlying capsule is incised from a cephalad end to a caudal end thereof, extending medial to the patient's patella.

3 Claims, 10 Drawing Sheets

METHOD OF PERFORMING A MODIFIED INTERVASTUS APPROACH IN TOTAL KNEE ARTHROPLASTY PROCEDURES

BACKGROUND

1. Field

The disclosure of the present patent application relates to surgical procedures, and particularly to a method of performing a modified intervastus approach in total knee arthroplasty procedures.

2. Description of the Related Art

During a total knee arthroplasty, an orthopedic surgeon removes diseased portions of bone in order to shape the remaining bone to accommodate a knee implant. During the procedure, the surgeon builds the artificial knee inside of the patient's leg, one component at a time, to create a highly realistic artificial joint. Although a wide variety of initial procedures exist for gaining access to the bone, each has its own difficulties and potentials for complications.

The most commonly used approach is the medial parapetellar approach, which is typically seen as being easy to perform, extensile, and easily repaired. However, this approach does not preserve the extensor mechanism and patients may not be able to actively extend their knee or perform straight leg raises soon after the surgery. Using the midvastus or subvastus approach typically permits straight leg raises more rapidly, however, these approaches are not easily extensile, are more difficult for many surgeons to perform, and are more challenging to close with a watertight seal.

The subvastus approach spares the quadriceps tendon and vastus medialis, however, as noted above, the approach is not extensile and may also be difficult to perform in obese and muscular patients, leading to longer operative time and blood loss. It also has the potential for an increased risk of subvastus hematoma, overstretching and ischemia of the vastus medialis, increased incidence of implant malpositioning, and possible detachment of the patellar tendon insertion. The midvastus approach, which separates the distal oblique portion from the proximal portion of the vastus medialis, is likely to damage the innervation of the muscle, which can affect quadriceps function and patellar tracking.

Thus, a method of performing a modified intervastus approach in total knee arthroplasty procedures solving the aforementioned problems is desired.

SUMMARY

The method of performing a modified intervastus approach in total knee arthroplasty procedures is an approach in which the arthrotomy is performed with elevation of the vastus medialis off of the underlying capsule. This elevation prevents dissection into either the quadriceps tendon or the vastus medialis muscle. Initially, a straight incision is made that is just medial to the midline, in line with the medial border of the tibial tubercle distally extending just proximal to the patella. This exposes the vastus medialis muscle and the interval between the quadriceps tendon and vastus medialis is then identified.

The fascia overlying the lateral edge of the vastus medialis is then incised where it meets the quadriceps tendon. The muscle is then sharply separated from its insertion onto the tendon and elevated bluntly off the underlying capsule, just enough to allow for later capsular repair. The underlying capsule is then incised from cephalad end to caudal end, extending medial to the patella. Closure may then be performed by repairing the capsule with absorbable suture, and then the vastus medialis fascia is repaired back to the very medial edge of the quadriceps tendon, restoring the anatomy.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of performing a modified intervastus approach in total knee arthroplasty procedures includes a modified intervastus approach for treating the anterior aspect of the knee. This approach minimizes a risk of dissecting the vastus medialis and the quadriceps tendon. The approach is relatively simple to perform, extensile (i.e., compatible with maneuvers such as a quadriceps snip, if required), and easily repaired at the end of the surgery.

Figure 1:
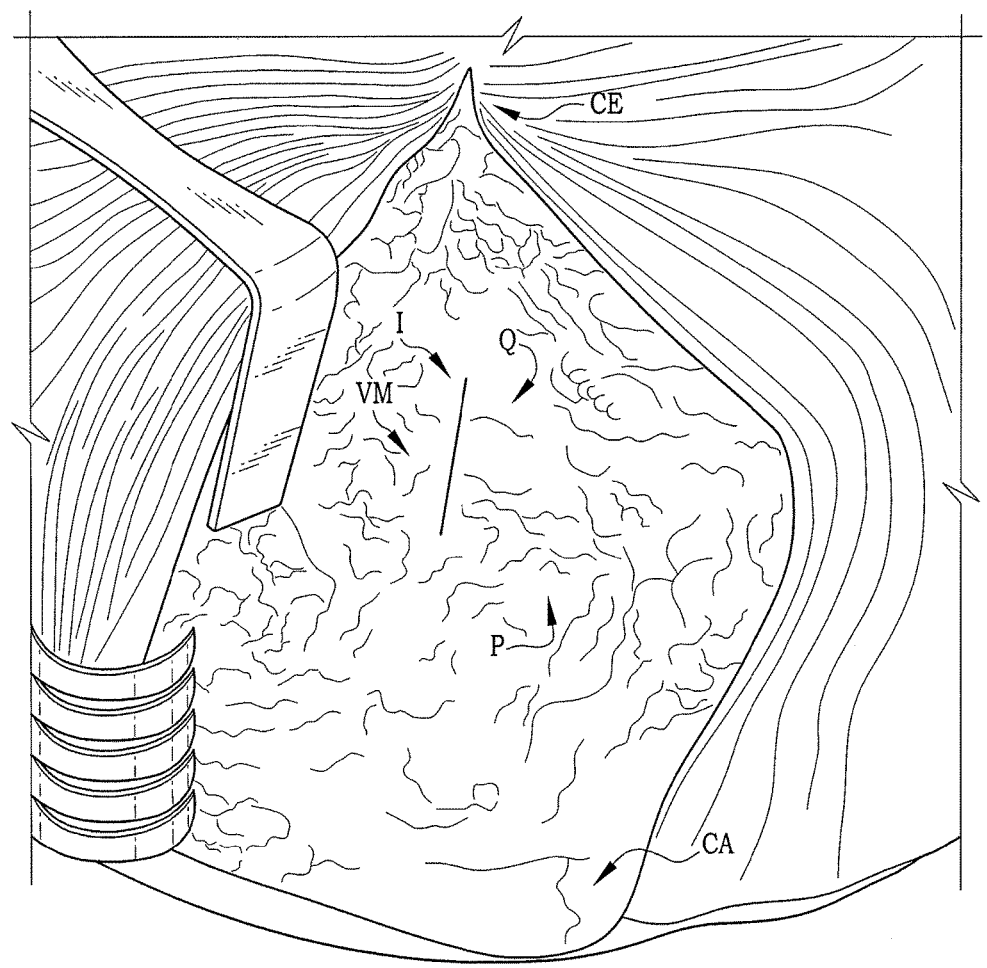
FIG. 1 illustrates an initial step of a method of performing a modified intervastus approach in total knee arthroplasty procedures.
Figure 2:
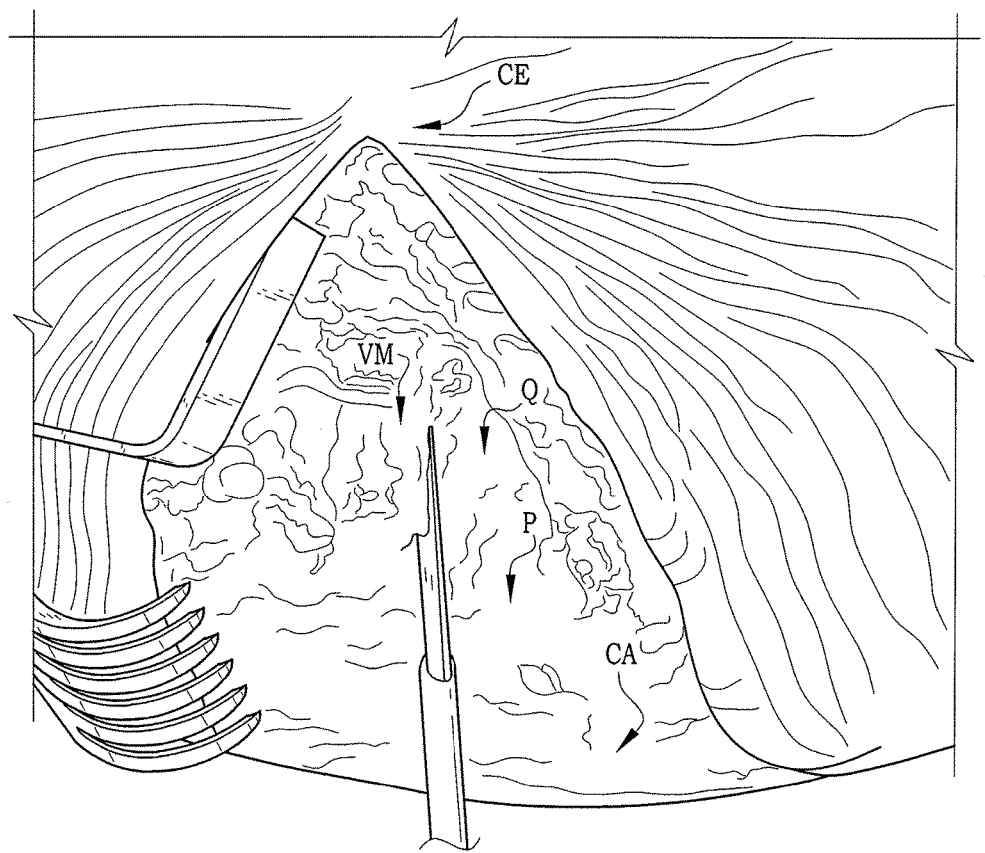
FIG. 2 illustrates a subsequent step of the method of performing a modified intervastus approach in total knee arthroplasty procedures in which a lateral edge of the patient's vastus medialis fascia is incised.
Figure 3:
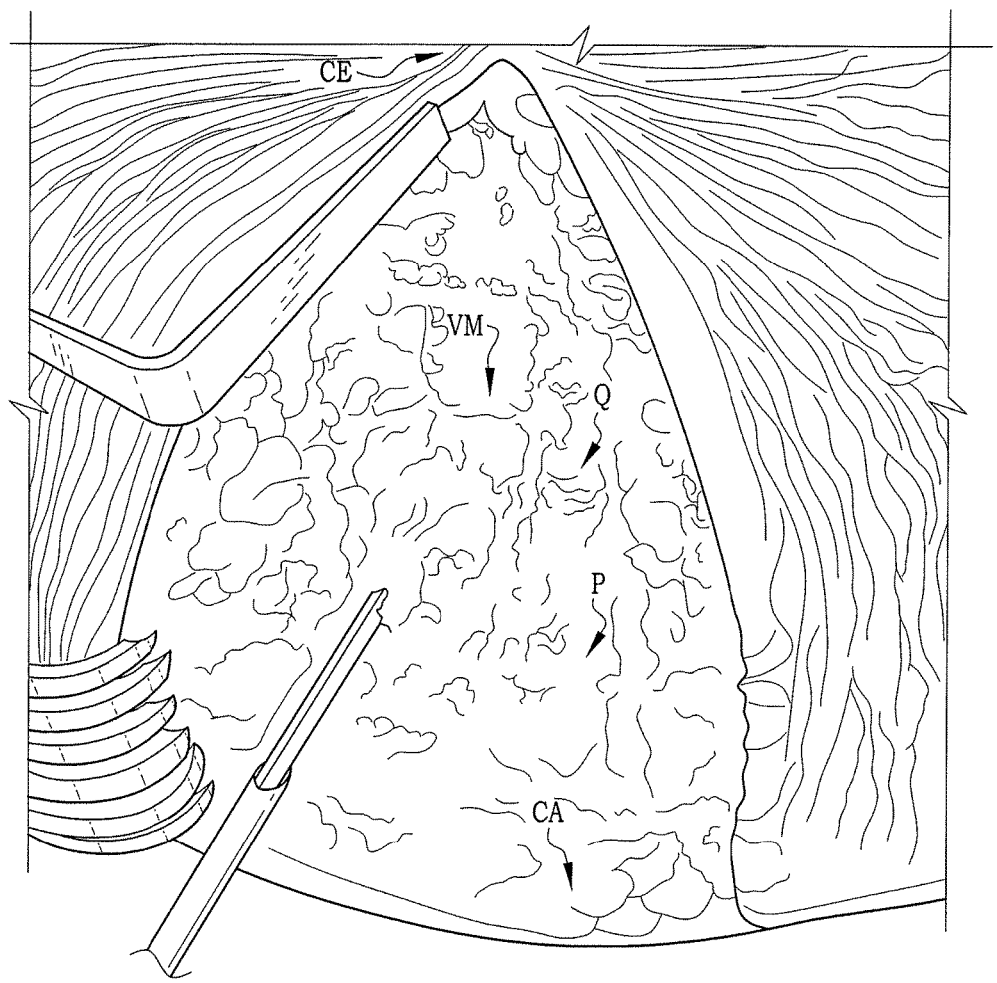
FIG. 3 illustrates a further subsequent step of the method of performing a modified intervastus approach in total knee arthroplasty procedures in which the patient's vastus medialis is elevated off of an underlying capsule.
Figure 7:
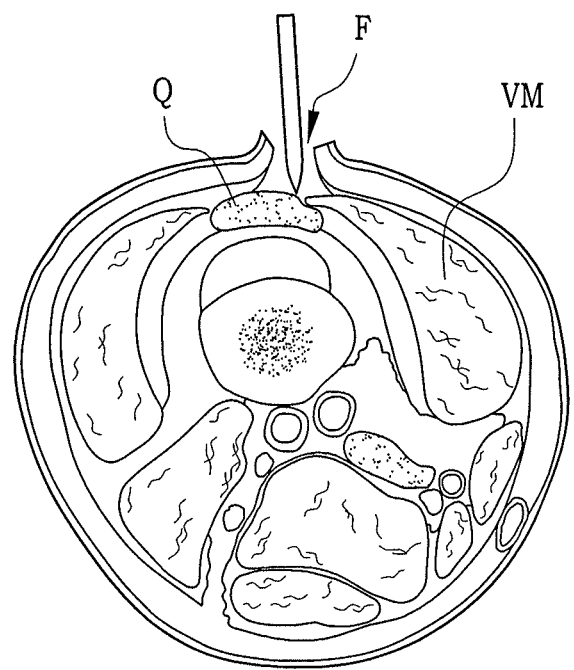
FIG. 7 is a cross-sectional view a patient's knee, illustrating, in cross-section, the steps of FIGS. 1 and 2 of the method of performing a modified intervastus approach in total knee arthroplasty procedures.
Figure 8:
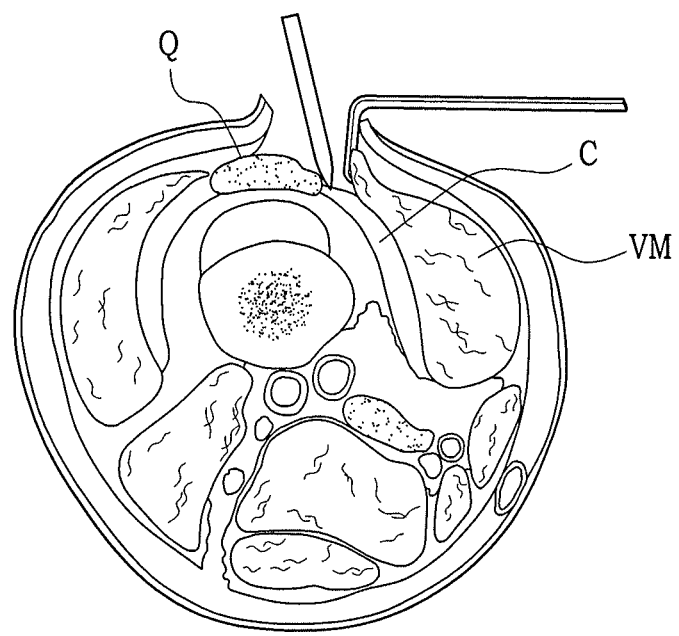
FIG. 8 is a cross-sectional view of the patient's knee, illustrating, in cross-section, the step of FIG. 3 of the method of performing a modified intervastus approach in total knee arthroplasty procedures.

The method of performing a modified intervastus approach in total knee arthroplasty procedures includes entering the knee at the junction between the quadriceps tendon and vastus medalis. The patient is positioned supine and a straight incision is made that is just medial to the midline, in line with the medial border of the tibial tubercle distally extending just proximal to the patella. Being just medial to the midline, in many cases, keeps the incision of the direct anterior aspect of the knee, which may facilitate kneeling. The subcutaneous tissues are dissected sharply, ensuring full thickness flaps to preserve the blood supply to the skin. In this manner, as shown in FIG. 1, the vastus medialis muscle VM is exposed and the intervastus interval I between the quadriceps tendon Q and vastus medialis VM is identified. The fascia overlying the lateral edge of the vastus medialis VM is incised where it meets the quadriceps tendon Q, as shown in FIG. 2. FIG. 7 shows a cross-sectional view of the incision of the vastus medialis fascia F. The vastus medialis VM is then elevated to expose the underlying capsule. As shown in FIG. 3, the muscle is sharply separated from its insertion onto the tendon and elevated bluntly off the underlying capsule, just enough to allow for a later capsular repair. FIG. 8 shows a cross-sectional view of blunt elevation of the vastus medialis VM to expose the underlying capsule C.

Figure 4:
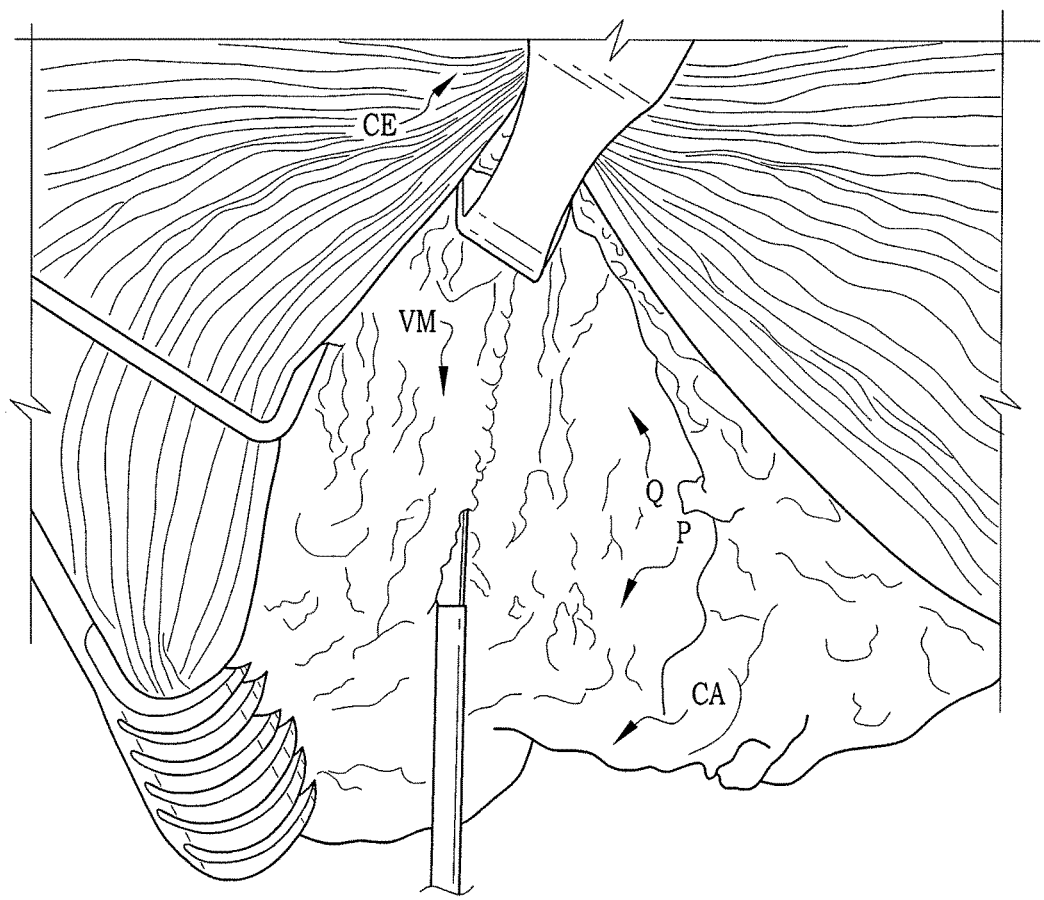
FIG. 4 illustrates a further subsequent step of the method of performing a modified intervastus approach in total knee arthroplasty procedures in which an arthrotomy is performed.
Figure 9:
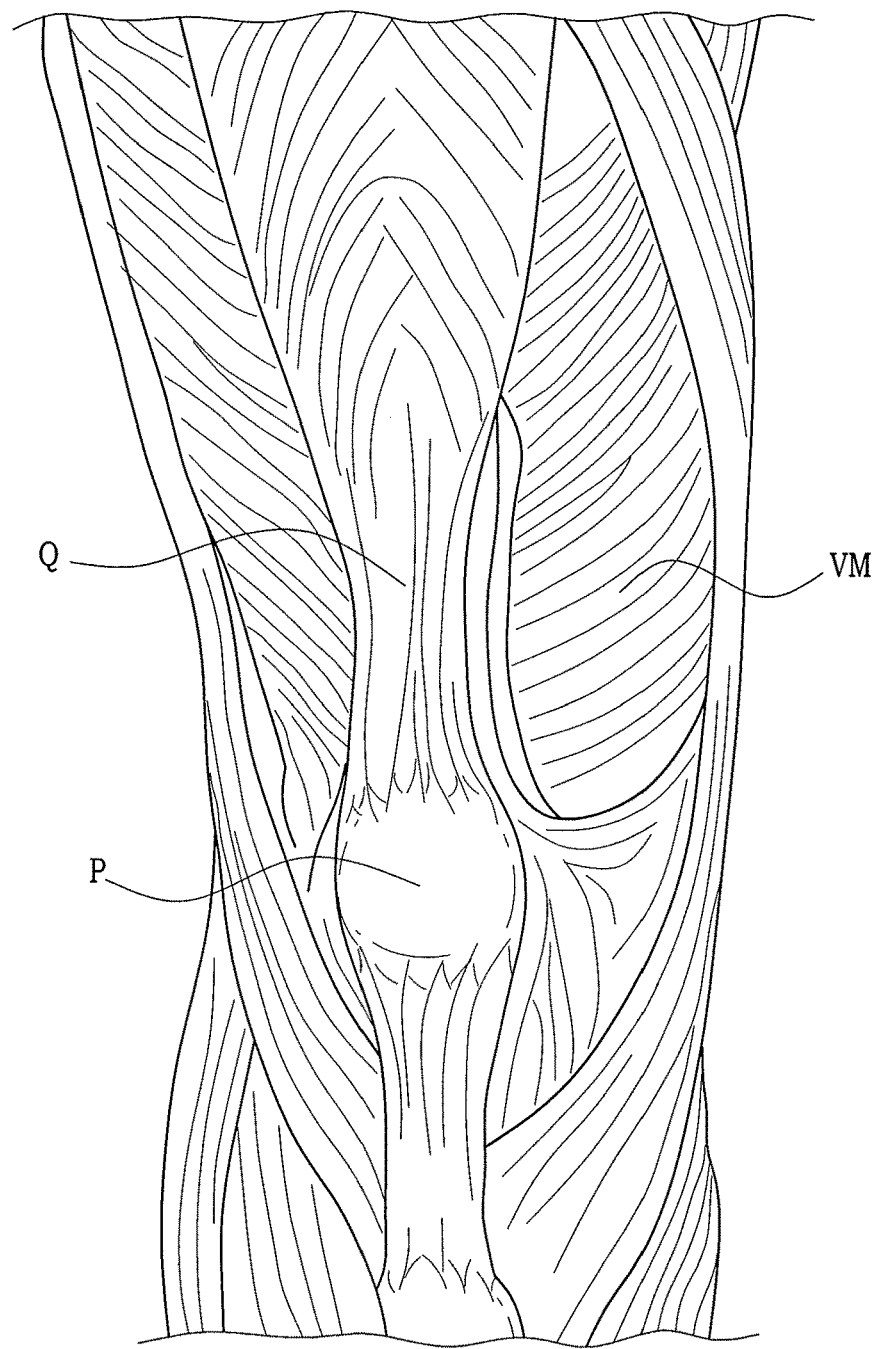
FIG. 9 illustrates the arthrotomy in the method of performing a modified intervastus approach in total knee arthroplasty procedures, particularly showing preservation of the quadriceps tendon and the vastus medialis.

As shown in FIG. 4, the underlying capsule is then incised from the cephalad end CE to the caudal end CA, extending medial to the patella P using the conventional technique used in the performance of medial parapatellar arthrotomy. This interval may be extended proximally between the vastus intermedius and the vastus medialis to expose the distal femur. During incision of the underlying capsule, a lateral capsular flap is left for closure. FIG. 9 illustrates the arthrotomy following elevation of the vastus medialis VM, specifically showing the preservation of the quadriceps tendon Q and vastus medialis VM.

Figure 5:
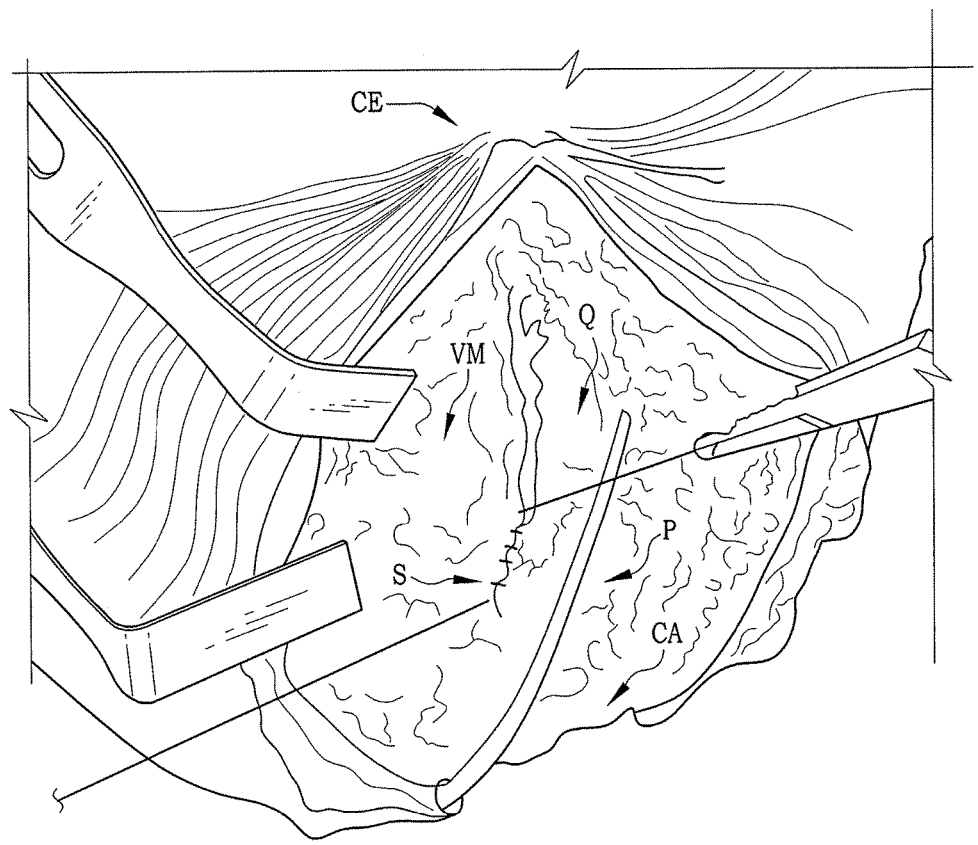
FIG. 5 illustrates a further subsequent step of the method of performing a modified intervastus approach in total knee arthroplasty procedures in which closure is performed via absorbale suture.
Figure 6:
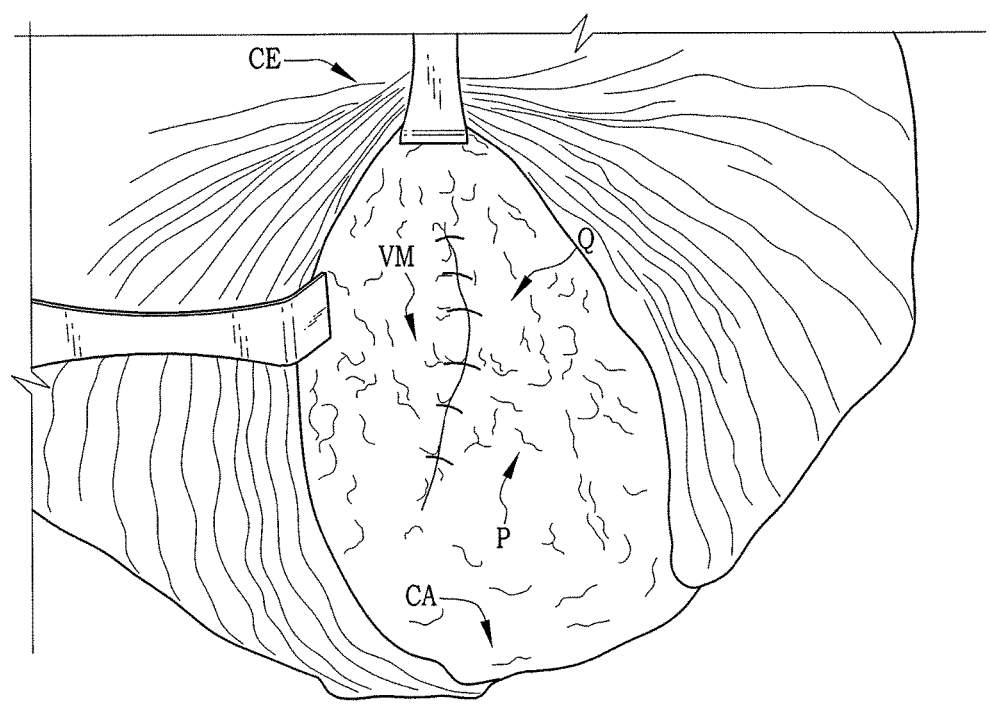
FIG. 6 illustrates a further subsequent step of the method of performing a modified intervastus approach in total knee arthroplasty procedures in which the capsule and the overlying vastus medialis fascia are repaired.
Figure 10:
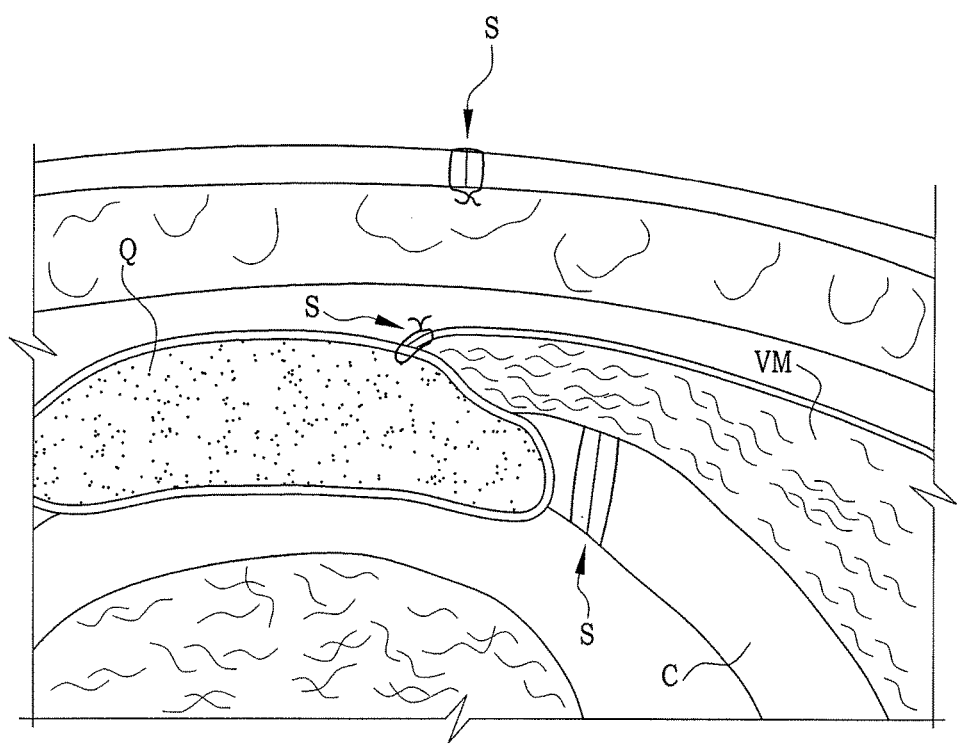
FIG. 10 is a cross-sectional view of the patient's knee, illustrating, in cross-section, the step of FIG. 6 of the method of performing a modified intervastus approach in total knee arthroplasty procedures.

Closure is performed by repairing the capsule with absorbable suture S, as shown in FIG. 5, and then the vastus medialis fascia F is repaired back to the very medial edge of the quadriceps tendon Q, restoring the anatomy, as shown in FIGS. 6 and 10.

As shown in FIG. 3, the incision is performed through interval I with elevation of the vastus medialis VM. Performing an arthrotomy through that interval without elevating the vastus medialis VM can lead to dissection into the quadriceps tendon Q and/or the vastus medialis muscle VM. This is even more likely in patients with a low lying vastus medalis. Thus, the method of performing a modified intervastus approach in total knee arthroplasty procedures as described herein ensures preservation of the extensor mechanism and vastus medialis VM by incising only the joint capsule which underlies the vastus medialis muscle VM. The method of performing a modified intervastus approach in total knee arthroplasty procedures can be performed relatively easily in either obese or muscular patients, does not require specialized instrumentation, and may be used with standard implants. For surgeons already familiar with the medial parapatellar approach, the method of performing a modified intervastus approach in total knee arthroplasty procedures requires very little further learning in surgical techniques, and is also an extensive approach which may be used in revision total knee replacements where the extensor mechanism is preserved, along with the vascularity and innervation to the vastus medialis VM.

Figure 11:
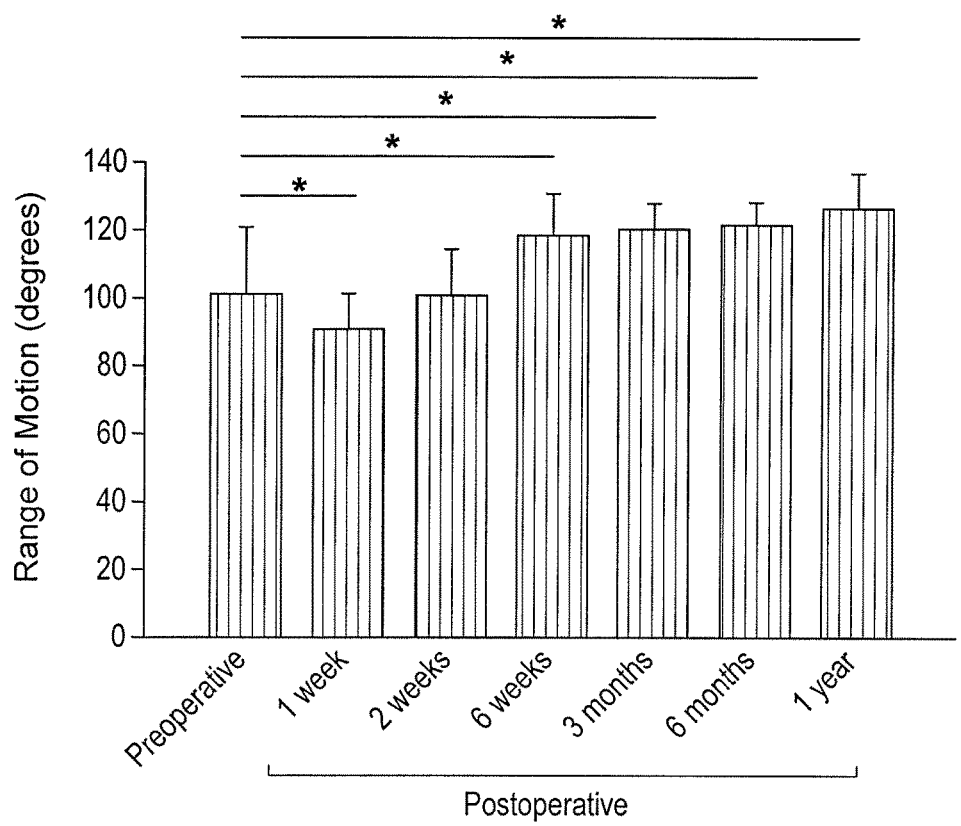
FIG. 11 is a graph comparing preoperative knee range of motion against knee range of motion at a variety of postoperative stages for the method of performing a modified intervastus approach in total knee arthroplasty procedures.

FIG. 11 shows a comparison between preoperative knee range of motion (ROM) against knee range of motion at a variety of postoperative stages (1 week, 2 weeks, 6 weeks, 3 months, 6 months and 1 year) for the method of performing a modified intervastus approach in total knee arthroplasty procedures. In FIG. 11, the "*" indicates a significant difference between time periods ($p<0.001$). Although knee ROM decreased significantly after one postoperative week, it began to increase at six weeks post-surgery. This trend continued up to the one year point.

It is to be understood that the method of performing a modified intervastus approach in total knee arthroplasty procedures is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of performing a modified intervastus approach in total knee arthroplasty procedures, comprising the steps of:
    making a straight incision in a patient's knee to expose the patient's intervastus interval between the quadriceps tendon and vastus medialis;
    incising fascia overlying a lateral edge of the patient's vastus medialis where the patient's vastus medialis meets the patient's quadriceps tendon;
    separating the patient's vastus medialis from the patient's quadriceps tendon along the intervastus interval;
    elevating the patient's vastus medialis off of an underlying capsule, thereby preserving the vastus medialis and quadriceps tendon;
    incising the underlying capsule from a cephalad end to a caudal end thereof so as to leave a lateral capsular flap to allow for subsequent repair of the lateral capsular flap during wound closure;
    repairing the underlying capsule with absorbable sutures; and
    repairing fascia of the vastus medialis to the medial edge of the quadriceps tendon.

2. The method of performing a modified intervastus approach in total knee arthroplasty procedures as recited in claim 1, wherein the straight incision comprises dissecting in line with the medial border of the tibial tubercle.

3. The method of performing a modified intervastus approach in total knee arthroplasty procedures as recited in claim 2, wherein the straight incision comprises sharp dissection of subcutaneous tissues.

* * * * *